(12) United States Patent
Collette (10) Patent No.: US 7,594,929 B2
(45) Date of Patent: Sep. 29, 2009

(54) ANCHORING SCREW FOR A RELAY STRIP OR SUTURE

(76) Inventor: Michel Collette, 11 avenue du Marechal, Brussels 1180 (BE)

( * ) Notice: Subject to any disclaimer, the term of this patent is extended or adjusted under 35 U.S.C. 154(b) by 549 days.

(21) Appl. No.: 10/535,724

(22) PCT Filed: Nov. 21, 2003

(86) PCT No.: PCT/IB03/06384

§ 371 (c)(1),
(2), (4) Date: Dec. 20, 2005

(87) PCT Pub. No.: WO2004/045465

PCT Pub. Date: Jun. 3, 2004

(65) Prior Publication Data

US 2006/0142769 A1    Jun. 29, 2006

(30) Foreign Application Priority Data

Nov. 21, 2002  (FR)  ................... 02 14597

(51) Int. Cl.
*A61F 2/06* (2006.01)
(52) U.S. Cl. ..................... 623/13.14; 606/53
(58) Field of Classification Search ..... 623/13.11–13.2; 606/53–73
See application file for complete search history.

(56) References Cited

U.S. PATENT DOCUMENTS

| 5,129,906 | A | | 7/1992 | Ross et al. |
| 5,300,076 | A | | 4/1994 | Leriche |
| 5,704,750 | A | * | 1/1998 | Bartos et al. ................. 411/411 |
| 5,713,904 | A | * | 2/1998 | Errico et al. ................. 606/327 |
| 5,716,359 | A | * | 2/1998 | Ojima et al. ................... 606/76 |
| 6,123,710 | A | | 9/2000 | Pinczewski et al. |
| 6,273,721 | B1 | * | 8/2001 | Valen ........................... 433/174 |
| 6,355,043 | B1 | * | 3/2002 | Adam ............................ 606/62 |
| 6,533,790 | B1 | | 3/2003 | Liu |
| 6,866,666 | B1 | * | 3/2005 | Sinnott et al. ................ 606/302 |
| 6,887,271 | B2 | * | 5/2005 | Justin et al. .............. 623/13.14 |
| 2003/0199878 | A1 | * | 10/2003 | Pohjonen et al. .............. 606/73 |

FOREIGN PATENT DOCUMENTS

| EP | 0 317 406 A1 | 5/1989 |
| EP | 0 651 979 A1 | 5/1995 |
| EP | 1 025 803 A1 | 8/2000 |
| FR | 2 717 070 | 9/1995 |
| FR | 2 732 211 | 10/1996 |
| WO | WO 95/15726 | 6/1995 |

* cited by examiner

*Primary Examiner*—Suzette J Gherbi
(74) *Attorney, Agent, or Firm*—Oliff & Berridge, PLC (57) ABSTRACT

The invention concerns an anchoring screw (1) in a bone tunnel (6) for a relay strip (8) made of synthetic material or a suture, comprising: a cylindrical proximal portion (3) of length ranging between 0 and 10 mm and a conical intermediate portion (4), whereon are provided a blunted thread (2) with a large pitch, the intermediate portion having a convergent section in the direction of, a smooth cylindrical distal portion at the rounded end and foam whereof the diameter is not less than the diameter of the bone tunnel (6).

7 Claims, 6 Drawing Sheets

ANCHORING SCREW FOR A RELAY STRIP OR SUTURE

The present invention relates to an orthopedic screw for fixing a ligament graft into a bone tunnel.

All the sports that involve twisting and turning such as rugby, football, skiing, etc. place great strain on the ligaments of the knee and therefore are in great danger of causing traumatic lesion. This danger is all the worse when these sports are practiced at a high level.

The short and thick anterior cruciate ligament runs obliquely from the prespinal surface of the upper face of the tibia to the axial face of the external condyle of the femur and provides the knee with rotary anterior stability.

Accidental tearing of the anterior cruciate ligament is one of the lesions most often encountered in sports injuries of the knee, often partially or fully incapacitating the casualty in terms of his or her chosen sport.

Nonetheless, there are surgical techniques for reconstructing the anterior cruciate ligament that allow the stability of the knee to be restored, thus restoring its functional capabilities.

An anterior cruciate ligament may be reconstructed by means of a ligament graft introduced into tibial and femoral bone tunnels, the articular orifices of which coincide with the zones of insertion of the natural anterior cruciate ligament.

Definitive anchoring of the graft is achieved by progressive adhesion and incorporation of the graft into the walls of the bone tunnel.

This incorporation occurs relatively quickly (in about six to eight weeks) if use is made of a graft taken from the ligamentum patellae comprising, at each of its ends, a small bony lump originating from the patella and from the tibia. This graft of the bone-tendon-bone type thus comprises a ligament central part and two bony parts, the latter allowing very good attachment into the bone tunnel.

This type of excision presents not insignificant potential disadvantages, namely weakening of the extensor system, residual pain, a risk of fracturing the patella or of tearing the ligamentum patellae, both of which are weakened by the excision to which they have been subjected.

In order to avoid these disadvantages, recourse may be had to ligament grafts taken from the tendons of the pes anserinus, that is to say the meeting of the terminal tendons of the sartorius, gracilis and semitendinosus muscles, known as a graft of the STG type.

This is actually a less invasive technique in which the risk of undesirable effects associated with the excision are far less high.

However, the graft thus formed is made of purely tendon tissue, that is to say tissue that has no bony lumps at its ends. This, by comparison with the bone-tendon-bone graft, presents a technical problem of attaching the graft to the bone tunnel.

It should be pointed out that it takes at least three months, and sometimes longer, for the inserted tendon tissue to adhere suitably to the wall of the bone tunnel. Throughout this time, the integrity of the set-up will therefore essentially rely on the quality of the artificial fixings installed during the intervention.

If the fixings of the graft are not effective enough, the repeated tensile forces associated with the knee regaining its mobility will cause the graft to slip gradually in the bone tunnel and lose its initial tension and relax into a slack state.

Various methods of attaching ligament grafts to a bone tunnel are known, each of them having, to various degrees, serious limitations.

One customary method of attachment is to introduce a screw known as an interference screw between the ligament graft and the wall of the bone tunnel in which the graft has already been introduced.

Experimentally, it has been possible to demonstrate that the mechanical pull-out strength of grafts of the "STG" type fixed by interference screws is of the order of 35-40 daN on average.

In some extreme cases, the mechanical pull-out strength may fail to exceed 20 daN.

Furthermore, the most recent experimental studies looking into the behavior of these grafts when subjected to cyclic tensile loadings in order to simulate what happens during re-education, show that this type of fixing is unable effectively to neutralize the progressive slippage of the graft that occurs at each tension spike. This slippage gives rise to a progressive loss in initial tension and may even, after a few hundred cycles, cause the graft to pull completely out of the bone tunnel.

Finally, the crushing of tendon tissue by the screw, all the more pronounced as the attachment is desired to be firm, may be very damaging to the histological evolution of the tendon tissue which runs the risk of being sheared, experiencing necrosis, and, ultimately, incorporating into the bone in a way which is sometimes extremely mediocre.

Another device aimed at avoiding the disadvantages of interference screws is to pass through the ligament loop a relay strip of synthetic fabric itself fixed onto a small metal bar (the endobutton type). Having passed through the entire bone tunnel along its longitudinal axis, pulling the relay strip and the ligament loop behind it, this bar pivots and presses against the bearing cortex and thus neutralizes any possible pulling-out of the graft.

This type of set-up makes it possible to obtain a strength which, according to the literature, does not, however, exceed 50 daN on average.

However, it has been clearly demonstrated that, when subjected to cyclic tensile forces, the relay strip deforms and gradually undergoes permanent elongation (this being all the more pronounced if its initial length is long) and this also leads to a progressive loss of the initial tension applied to the graft at its time of insertion.

Now, it is acknowledged that the movements of the knee during everyday life and, as a result, during free re-education exercises, give rise to cyclic tension spikes in the cruciate ligament or in its substitute, which may be as high as 50 daN.

What that means is that allowing the patient to undertake intensive and early re-education, which is an increasingly pressing demand from patients who are sportsmen and -women, after the anterior cruciate ligament has been reconstructed, very obviously entails risks of damaging the mechanical properties of the graft namely of causing a relapse into the slack state or a risk of accidental tearing out.

These risks of damage to the fixing to a bone tunnel, which are already very real in the case of the use of a graft of the "bone-tendon-bone" type, are even greater when using a graft of the "SGT" type even though the latter is far more advantageous from the point of view of the secondary disadvantages associated with the excision.

An object of the invention is therefore to propose a device for fixing a ligament graft into a bone tunnel which has good resistance to tension in order to limit the risks of the ligament graft being pulled out of or slipping in a bone tunnel.

To this end, the invention relates to an anchoring screw for anchoring a relay strip made of synthetic material or a suture in a bone tunnel, having:

- a cylindrical proximal part with a length of between 0 and 10 mm, and a conically tapered intermediate part, on both of which a blunted screw thread with a long pitch is formed, the intermediate part having a cross section that tapers towards
- a plain cylindrical distal part with a rounded and blunt end, the diameter of which is at least equal to the diameter of the bone tunnel.

The screw according to the invention therefore comprises three distinct parts: a proximal part of cylindrical cross section, an intermediate part of conically tapering cross section and finally the distal part of cylindrical cross section the end of which is rounded and blunt. The screw comprises a large blunted and non-damaging screw thread running exclusively along the proximal and intermediate parts.

This configuration allows this screw to perform optimally its role of immobilizing a textile relay strip against the wall of the bone tunnel in which a helical screw thread will have been made in advance using a tap.

The textile relay strips are then passed through the bone tunnel, pulling the ligament loop along behind them. Once the graft is in place, the screw is introduced between the two strands of the relay strip and immobilizes it by pressing it firmly against the threads in the bone without the risk of damaging the relay strip thanks to the rounded and blunt shape of the screw thread.

The relay strip, because of its flexibility, can deform and closely hug the crenellated relief of the helical screw thread formed in the wall of the bone tunnel.

The conically tapering shape of the screw will give rise to an effect of crushing the relay strip against the bone wall to an extent that increases with the depth to which the screw is introduced.

The taper of the screw is maintained, however, only over its intermediate part. This is because a screw that was tapered along its entire length would carry the risk of giving rise to a wedge effect likely to cause the bone to split open as it progressed into the bone tunnel.

The distal part of the screw, which is cylindrical and has a rounded end, corresponds to the region of transition between the fixed part of the relay strip fixed by the thread of the screw against the screw thread in the bone, and the free part thereof that passes through the ligament loop. It is in this region that the back and forth micromovements of the tape against the bone occur during the cyclic tension-release cycles induced in the graft as the knee moves. This is why this distal region is entirely plain and smooth and devoid of screw thread so as to prevent any risk of the relay strip being sheared during the back and forth micromovements against the bone wall.

According to a preferred embodiment of the screw, the pitch, between two consecutive threads is equal to approximately 5 mm, which corresponds to the space needed for the suspension relay to be able to deform freely and closely hug the crenellations of bone created by the tap.

According to a preferred possibility, the cylindrical distal part has a length of more or less 5 to 6 mm. This distance is needed to neutralize the back and forth micromovements of the tape against the bone during cyclic tensions on the graft and thus avoid the risks of shearing that would definitely occur if the screw thread extended as far as the distal end of the screw.

In order to fit the screw, the proximal face thereof has a hexagon socket.

As a preference, the screw thread has a thread depth of between 1 and 3 mm, and preferably of 1.5 mm, so as both to fix the screw into the bone tunnel and to immobilize the relay strip.

For a clear understanding thereof, the invention is described with reference to the drawing which, by way of nonlimiting example, depicts one embodiment of the screw according to this invention.

Figure 1:
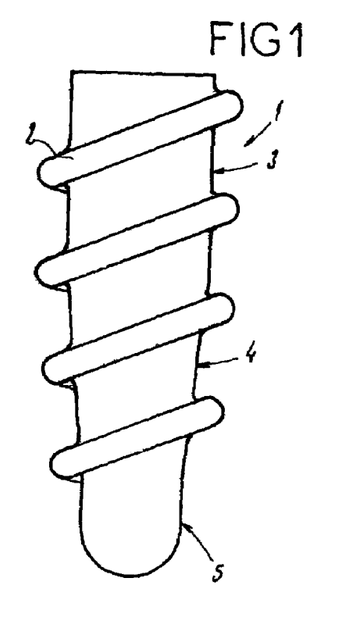
FIG. 1 is an external view of the screw.

As can be seen in the drawing, the screw 1 has a cylindro-conical overall shape with a helical screw thread 2. It is made of metal, for example of titanium or of stainless steel. It may equally be made of a biodegradable material, such as a lactic acid copolymer.

The screw has three distinct parts: a proximal part 3 of cylindrical section, about 10 mm long, an intermediate part 4 of conically tapering cross section, also about 10 mm long, and finally a distal part 5 of cylindrical shape with a rounded and blunt end, measuring about 5 mm in length.

The screw thread 2 extends over the proximal and intermediate part of the screw, and not over its distal part.

This screw thread 2, as shown by the figures, is blunted and has a long pitch. In the example depicted, the pitch, which separates two consecutive threads, is about 5 mm. It will also be noted that the screw thread 2 is very deep, the depth being between 1 mm and 3 mm, and preferably 1.5 mm.

In practice, this screw is used as follows.

The intervention begins with the excision of a ligament from the semitendinosus using conventional instruments (stripper) and the graft 12 is left to one side.

Figure 4:
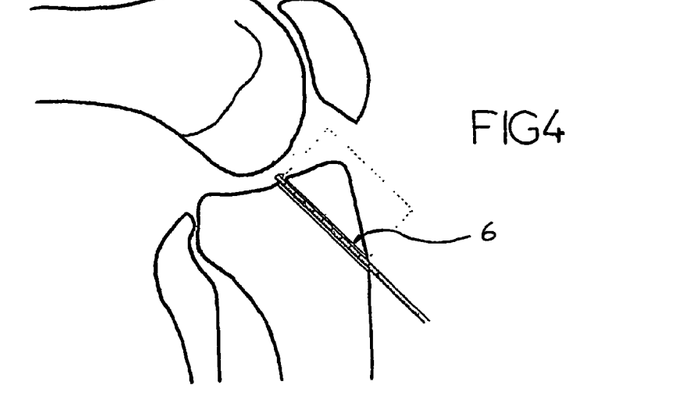
FIGS. 4 to 9 depict the various steps in the method of reconstructing an anterior cruciate ligament using the screw that is the subject of the invention.

Next, under endoscopic control, a graft insertion tunnel 6 is made through the tibia. This phase of the intervention is depicted in FIG. 4. In a way that is entirely conventional, a guide pin, the end of which reaches the tibial point of insertion of the anterior cruciate ligament is introduced through the bone. Conventional monitors available on the market may be used for this. A 4.5 mm cannulated drill bit introduced from outside inwards, guided by the pin producing the tibial tunnel. The length of the tunnel is then measured.

In the same way, arthroscopy is used to select the point of attachment of the graft to the femur and, at this point, a guide pin is introduced from the inside of the knee outwards. This introduction of this pin may be performed either via the tibial tunnel (possibly adjusting the axis of penetration by varying the degree of flexion of the tibia) or via the antero-internal arthroscopic approach.

It is also possible, by using a monitor intended for that, to introduce the pin from outside inwards, according to the operating surgeon's preferences.

Like with the tibia, a tunnel approximately 4.5 mm in diameter is then made using the same hollow drill bit sliding along the femoral guide pin. The length of the femoral tunnel L1 and the distance separating the two, femoral and tibial, intra-articular orifices L2 (the intra-articular length of the graft) are measured.

The most appropriate length of fixing screw and the depth of bone housings to be produced in order to accommodate the graft can then be selected according to the length of the bone tunnels. The maximum length of the graft will need to correspond to the sum of the depth of the two housings (femoral and tibial) and the intra-articular length L2.

The graft can then be prepared to the dimensions thus measured.

Figure 10:
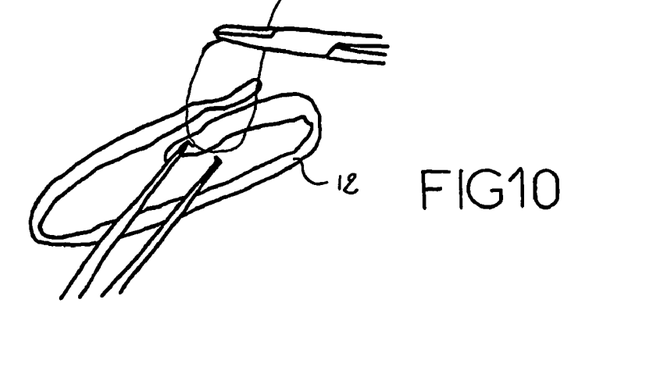
FIGS. 10 to 13 depict the steps of constructing a graft to be substituted for the anterior cruciate ligament.
Figure 11:
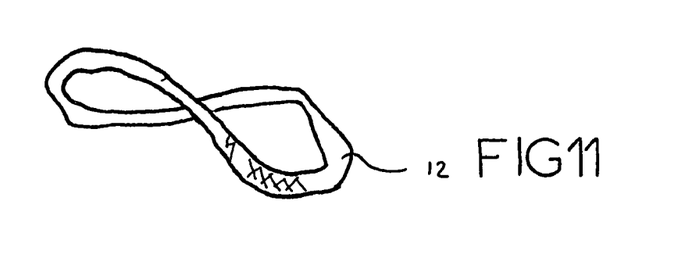
Figure 12:
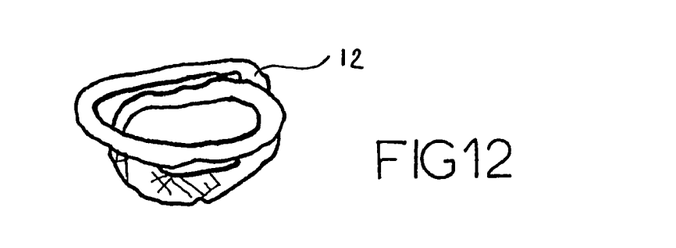

One way of preparing the graft 12 is to excise a tendon, preferably the semitendinosus. The two ends of the graft 12 are then attached to one another to form a closed loop (the size of which is twice the desired size of the final graft) as shown in FIG. 10. The graft is then twisted on itself into a figure-of-eight shape (see FIG. 11) then folded onto itself to obtain a four-strand closed loop comprising a single suture, the graft 12 in this configuration is depicted in FIG. 12.

Another way of preparing the graft is to wind it around two pivot markers the separation of which corresponds to the final dimension of the graft. One or two ligatures produced at each end of the graft provide a very easy and effective way of neutralizing any possible slippage of the strands of ligament with respect to one another and a graft 12 which is extremely strong in tension is thus very soon obtained.

Each end of the graft 12 is calibrated with a view to determining the diameter of bone housings to be produced.

Figure 13:
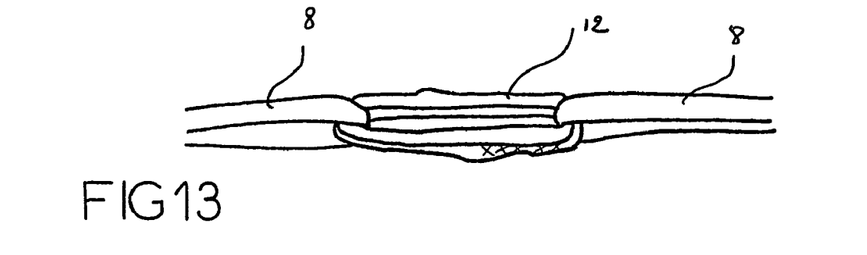
Figure 14:
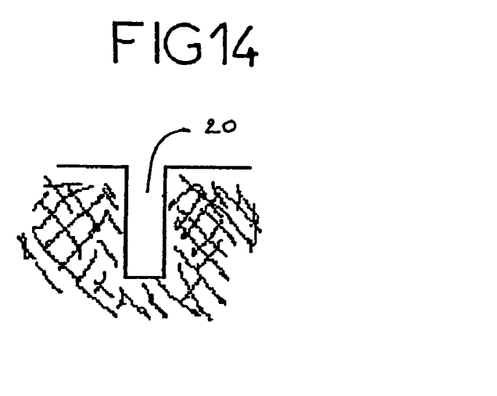
FIGS. 14 to 17 depict another embodiment of the screw.
Figure 15:
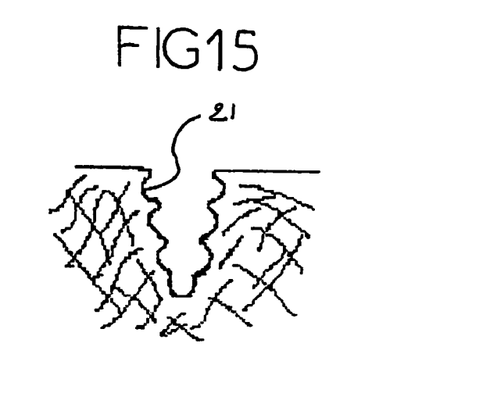
Figure 16:
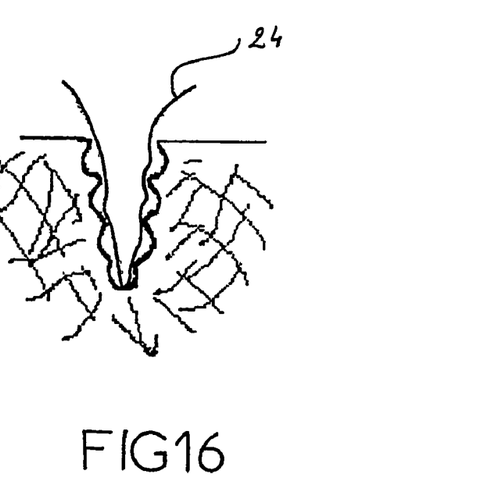
Figure 17:
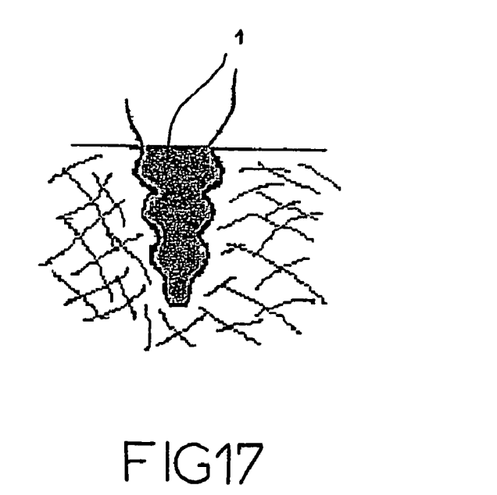

Two relay tension strips 8, each 40 or 50 cm long, are slipped through the ligament graft and wrap around each tension pole thereof, as depicted in FIG. 13. The relay strips 8 may be made of a synthetic material such as a polyester terephthalate. One example of this material used in surgery is Mersilene. The relay strips 8 are about 7 mm wide.

The strips 8 are fixed to the pulling posts of a stretcher the spring of which is calibrated to exert continuous tension of about 40 daN. This tension will be exerted on the graft 12 throughout the preparation of the bone tunnels so as to neutralize any plastic deformation of the graft and of the textile material of which the relay strips 8 are made which could occur gradually as the system is being tensioned.

The tibial and femoral bone housings are then prepared, with the diameter and depth determined previously.

In the femur, the housing may be produced in the conventional way using a graduated and cannulated auger introduced via the antero-internal arthroscopic approach and guided along a guide pin introduced into the femoral tunnel via the same approach.

Figures 5, 6:
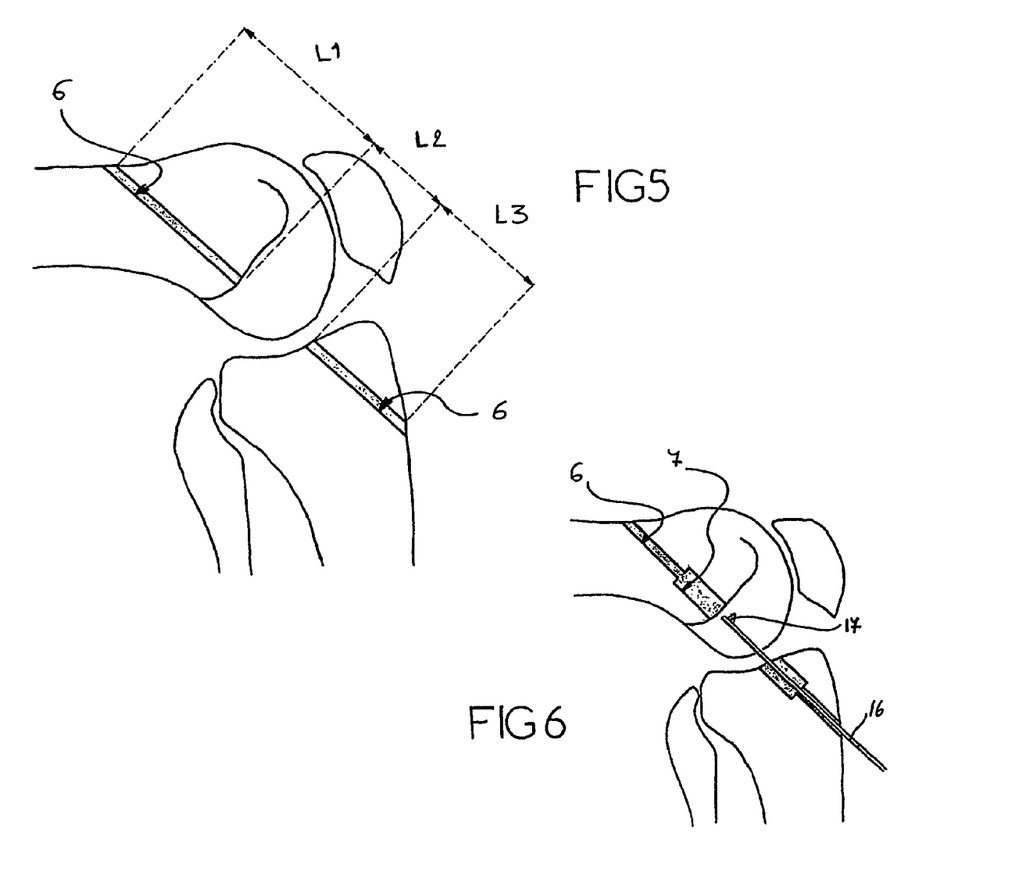

This housing could equally be produced using a special auger introduced via the tibial tunnel, as can be seen in FIG. 6.

This instrument consists of a hollow tube with a diameter slightly smaller than 4.5 mm, equipped at its end with a fine cutter in the shape of a wing. A guide pin 16 introduced into the tibial tunnel allows the auger, which is tapped in with a hammer from outside the tibia towards the articular cavity, to be guided. The cutter 17 of the auger creates, in the bone through which it passes, a small intra-osseous groove of little significance until it reaches the actual site of the articular cavity, where the instrument can then turn freely and create a housing 7, either a femoral housing (by moving forwards) or tibial housing (by moving backwards), the diameter of which corresponds to twice the radius of the auger and of its cutter 17.

It is also possible to conceive of boring out the tibial housing 7 using an auger composed of a fine handle and of an end corresponding to the desired diameter for the tibial housing. This auger would be introduced via the antero-internal approach, the fine handle sliding along a guide pin placed in the femoral tunnel. Once the auger had been completely introduced into the knee, by varying the degree of flexion, the axis of the tibial and femoral tunnels could once again be made to coincide so that the guide pin could be introduced into the tibial tunnel from inside the knee and the housing then produced simply by turning the auger on this pin inside the tibia until the desired depth was reached. Another possibility could consist in introducing a fine handle into the tibial tunnel from the outside inwards, then, via the antero-internal approach, introducing a cutting instrument of the desired diameter designed to be articulated with the tibial handle which would then also actuate the cutting part backwards.

Figure 7:
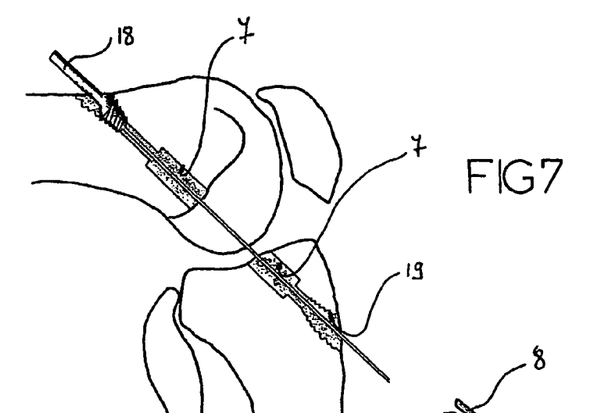

The preparation of the bone tunnels 6 ends with the introduction of a tap 18 intended to prepare a screw thread 19 for the fixing screw. This operation is depicted in FIG. 7.

This tap is introduced into the femur from outside inwards through a short incision in the skin measuring 1 to 2 cm. Its direction is dictated by the guide pin introduced into the femoral tunnel 6.

In the same way, the tap 18 is introduced into the tibia from the outside inwards and also slides along the guide pin.

Figure 8:
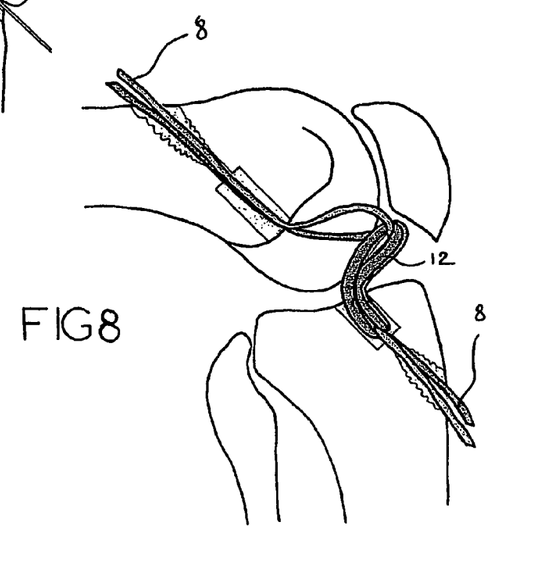
Figure 9:
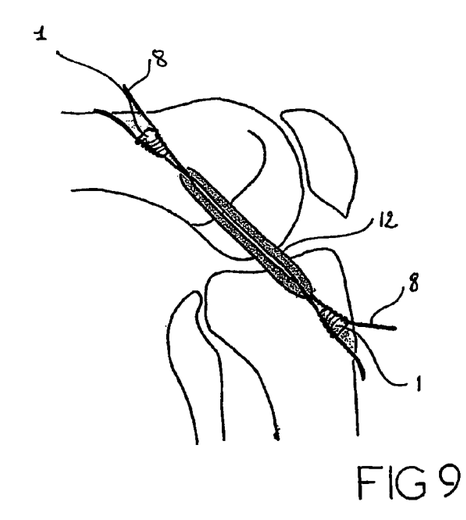

The tension strips 8 for pulling the graft 12 are introduced via the antero-internal approach, pulled into the femoral and tibial bone tunnels 6 by means of a simple pulling filament in the form of a lasso and then recovered on the outside of the knee, as can be seen in FIG. 8.

A fine metal filament running through the proximal pole of the graft and emerging between the two pulling strips is passed through the femoral tunnel at the same time as the strips. The other end of the filament emerges via the antero-internal approach.

This metal filament will allow the fixing screw 1 to be guided as far as the entrance to the bone tunnel without a surgical approach having to be made in the femur.

The graft 12 is pulled into the femoral housing simply by pulling on the relay strips 8. The screw 1 is then introduced into the tunnel 6 where it is guided by the metal filament. As soon as the screw finds its housing, the filament can be removed simply by pulling it.

The pulling of the strips 8, on the tibia side, completes the introduction of the graft into the tibial housing 7.

The position and the tension of the graft 12 are checked endoscopically prior to the final locking operation which is carried out using the tibia screw 1.

If the tension is not satisfactory, the tibia screw 1 can be withdrawn, tensioning resumed, and locking obtained once again by fully introducing the screw 1. The relay strips 8 are then cut off flush with the screw 1. That is performed under the control of the view at the tibia and by means of an instrument of the guillotine type at the femur.

Figure 2:
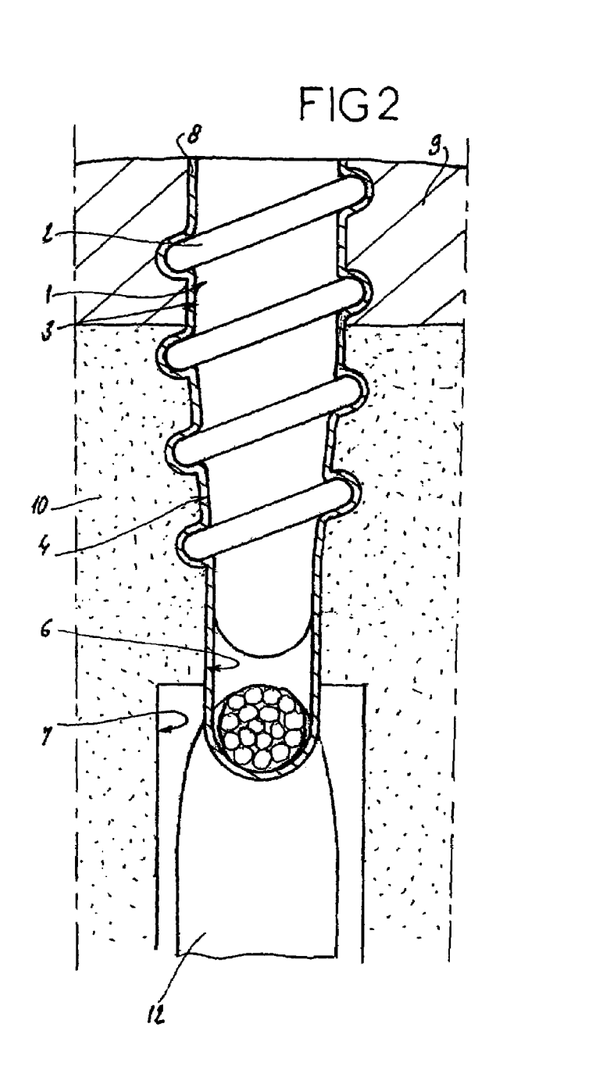
FIG. 2 depicts the screw in place in the bone tunnel and retaining a ligament graft.
Figure 3:
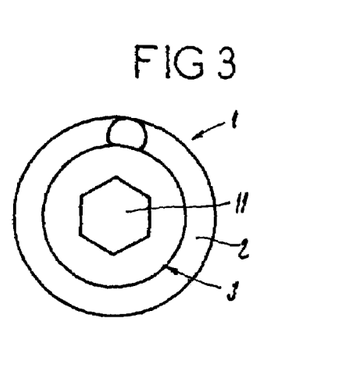
FIG. 3 depicts the proximal face of the screw.

FIG. 2 shows the ligament graft 12 in place in the bone housing 7 and suspended by the synthetic relay 8 pressed firmly by the screw 1 against the screw thread formed in the wall of the bone tunnel. It can be seen that the graft is fixed partially in the cortex region 9 and partially in the spongy region 10 of the bone.

The invention thus provides an anchoring screw for anchoring a ligament graft in a bone tunnel that has the numerous advantages mentioned above.

First of all because of the pulley effect created by the use of a ligament graft in a closed loop with four strands: the tensile force introduced into the graft will be quartered at the suture.

Secondly, as the synthetic relay strips 8 pass freely through the ligament loop, the tensioning of these strips will allow the force to be automatically distributed equally through each of the strands that make up the graft.

Thirdly, the use of relay strips 8 makes it possible to obtain a firm attachment while at the same time avoiding the risk of damaging the ligament tissue by crushing it forcibly against the wall of the tunnel.

Fourthly, the tensile strength afforded by a flexible relay strip 8 fixed by interference screws is far greater than that obtained by the traditional methods. Tests carried out in a mechanical laboratory have shown that the pull-out strength of a 7 mm Mersilene tape fixed into human bone using a screw according to the invention varied with the specimens (according to the bone quality) between 120 and 220 daN, namely three or four times higher than the strength obtained with conventional interference screws. This strength greatly exceeds, and this is true for all individuals, the 50 daN peaks of tension that the graft will have to withstand during free re-education exercises. Cyclic tensile testing evaluating means of attachment of ligament grafts commonly used (interference screws, stirrup pieces, etc.) have shown that during tests at 45 daN, the best specimens were unable to withstand more than 200 to 300 cycles. By contrast, with a 7 mm Mersilene strip held by the screw that is the subject of the invention, cyclic tensile tests comprising rounds of 600 tension cycles varying from 2.5 to 25 daN alternating with rounds of 600 tensile cycles varying from 5 to 50 daN demonstrated that, after 33 800 cycles, the specimens showed no perceivable sign of degradation of their mechanical properties (rigidity, pull-out strength).

A fifth advantage of the use of relay strips 8 is a saving on the amount of tendon tissue that has to be excised to form the graft, because the fixing is performed by means of synthetic tissue rather than by means of the tendon itself as was the case in the traditional techniques. That means that the tissue removed is shorter, and therefore causes markedly less trauma.

It goes without saying that the invention is not restricted to the embodiment described hereinabove by way of nonlimiting example but that, on the contrary, it encompasses all embodiment variants thereof. The screw may, for example, exist with other sizes so as to meet the mechanical and physiological requirements of particular cases.

Thus, it would also be possible to anticipate using the screw according to the invention for fixing not a synthetic strip but sutures into a bone, for the attachment of soft tissue.

This use of the screw is illustrated in FIGS. 14 to 17. In this use, a blind hole 20 is pierced in a bone, a screw thread 21 is then made in the wall of this hole. A suture 24 is pushed into the bottom of the hole 20, the suture 21 is then locked in place by a screw 1 according to the invention. This use of the screw makes it possible to avoid the use of fixing anchors, one example of which is illustrated by document WO 95/15726.

The disadvantages of these anchors are, on the one hand, that they are expensive and, on the other hand, that when one of the sutures breaks, the entire anchor has to be replaced.

In this embodiment, the screw of course has suitable dimensions generally very much smaller than those of the screw used in the case of the reconstruction of a knee.

Another possible embodiment of the screw is depicted in FIGS. 18 to 21 in the case of desinsertion of a ligament.

Figure 18:
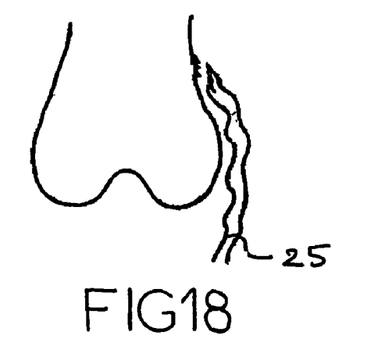
FIGS. 18 to 21 depict another embodiment of the screw.

FIG. 18 depicts a case of desinsertion of a ligament, that is to say the tearing of the point of attachment of a ligament 25 to a bone.

A tunnel 26 through the bone is made at the point of ligament desinsertion and a housing 27 for the screw is prepared percutaneously.

Figure 19:
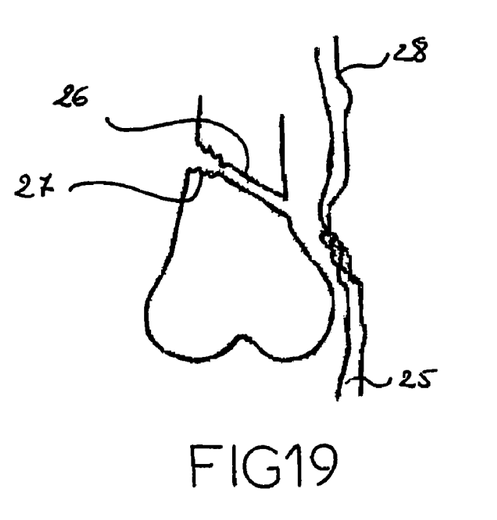

A lacing of sutures 28 is performed in the end of the ligament 25 that is to be reinserted, as can be seen in FIG. 19.

The sutures 28 are then passed through the bone tunnel then recovered through a miniscule incision in the skin.

Figure 20:
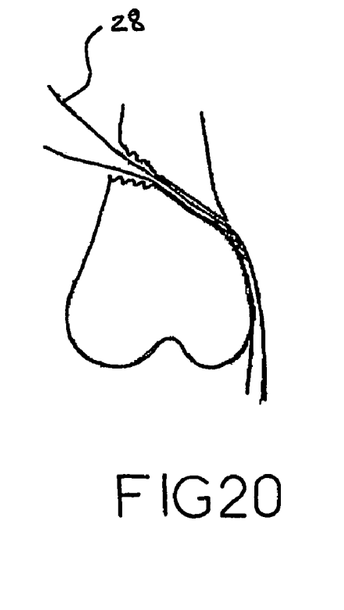

Pulling of the sutures 28 re-tensions the ligament 25 at the entry to the bone tunnel 26 as can be seen in FIG. 20.

Figure 21:
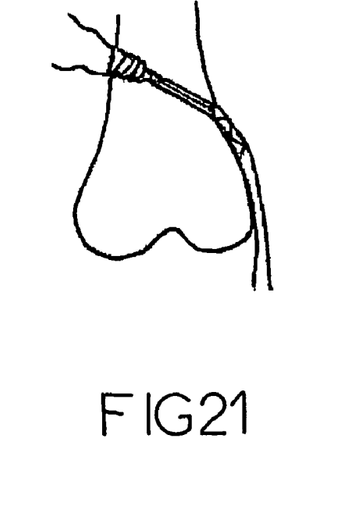

The screw 1 is then introduced percutaneously and locks the sutures 28 (see FIG. 21).

This use of the screw is therefore not very invasive and eliminates the need to produce attachment knots something which, in practice, may prove technically difficult and dictate a surgical approach on the external face of the bone.

It should be noted that in the case of short tunnels in bone, the cylindrical part of the screw may be shortened or nonexistent, that is to say of zero length. In this case, the taper of the intermediate part may be accentuated and the distal part may also have its length reduced.

The invention claimed is:

1. A method for fixing a ligament graft into a bone tunnel, the method comprising:
    making a graft insertion tunnel in a tibia and in a femur and making a helical screw thread in each of the tunnels;
    preparing a ligament graft having a plurality of poles to an appropriate dimension and forming a multiple strands closed loop;
    slipping at least one relay tension strip through each of the poles of the graft;
    passing one of the relay strips through the tunnel in the tibia and another of the relay strips through the tunnel in the femur and pulling the graft along behind the relay strips; and
    introducing a screw between two strands of each relay strip and immobilizing each one of the relay strips by pressing the screw against a respective one of the helical screw threads in each of the tunnels made in a bone,
    the screw comprising:
        a cylindrical proximal part with a length of between 0 and 10 mm;
        a conically tapered intermediate part; and
        a blunted screw thread with a long pitch formed on both the cylindrical proximal part and the tapered intermediate part;
    wherein the tapered intermediate part has a cross section that tapers towards a plain cylindrical distal part with a rounded and blunt end, a diameter of the cylindrical distal part is at least equal to a diameter of a bone tunnel.

2. The method as claimed in claim 1, wherein the method of preparing the ligament graft comprises:
    excising a ligament from the semitendinosus to obtain the graft;
    attaching two ends of the graft to one another to form a closed loop;
    twisting the closed loop on itself into a figure-of-eight shape; and
    folding the shape onto itself to obtain a four-strand closed loop comprising a single suture.

3. The method as claimed in claim 1, wherein prior to the insertion of the graft through the bone tunnels, the relay strips are fixed to pulling posts of a stretcher, the stretcher having a spring calibrated to exert continuous tension of about 40 daN.

4. The method as claimed in claim 1, further comprising preparing a bone housing in the tibia and in the femur for receiving each one of an end of the graft, each bone housing being calibrated according to the previously measured diameter of each graft's end.

5. The method as claimed in claim 4, wherein the femoral or the tibial housing is produced using an auger equipped with a cutter, the auger being introduced via a femoral or tibial tunnel from outside towards the articular cavity and creating a small intra-osseous groove when guided in the femoral or tibial tunnel before reaching an actual site of an articular cavity, where the auger can then turn freely and create a housing into the bone by moving forwards or backwards.

6. The method as claimed in claim 1, wherein the method of making the helical screw thread in the femur or in the tibia comprises introducing a tap into the femur or the tibia from outside inwards through a short incision in a skin, the tap direction being dictated by a guide pin introduced into the femoral tunnel.

7. The method as claimed in claim 1, wherein the method of preparing the ligament graft comprises:
    excising a ligament from the semitendinosus to obtain the graft;
    winding the ligament around two pivot markers separated from one another by a distance equal to the final dimension of the graft; and
    providing one or more ligatures at each end of the graft.

\* \* \* \* \*